(12) United States Patent
Povolosky et al.

(10) Patent No.: US 9,950,190 B2
(45) Date of Patent: Apr. 24, 2018

(54) DEVICE AND METHOD OF TREATING FUNGAL NAIL INFECTIONS

(71) Applicants: Medical Quant LTD, Kfar Saba (IL); M.B. Mazor Consulting and Services Ltd, Hod Hasharon (IL); Gadi Presburger, Tel Aviv (IL); Asaf Tenne, Yahud (IL); Amos Thein, Yahud (IL)

(72) Inventors: Moshe Povolosky, Kfar Saba (IL); Gal Elchanan Gotlieb, Ra'anana (IL)

(73) Assignees: MEDICAL QUANT LTD, Kfar Saba (IL); M.B. MAZOR CONSULTING AND SERVICES LTD, Hod Hasharon (IL); Gadi Presburger, Tel Aviv (IL); Asaf Tenne, Yahud (IL); Amos Thein, Yahud (IL)

( * ) Notice: Subject to any disclaimer, the term of this patent is extended or adjusted under 35 U.S.C. 154(b) by 402 days.

(21) Appl. No.: 14/142,050

(22) Filed: Dec. 27, 2013

(65) Prior Publication Data

US 2014/0194955 A1    Jul. 10, 2014

Related U.S. Application Data

(63) Continuation-in-part of application No. PCT/IB2012/053352, filed on Jul. 2, 2012.
(Continued)

(30) Foreign Application Priority Data

Dec. 27, 2012    (GB) .................................. 1223438.1

(51) Int. Cl.
  *A61N 5/067*    (2006.01)
  *A61N 5/06*    (2006.01)
  *A61N 2/00*    (2006.01)

(52) U.S. Cl.
  CPC .......... *A61N 5/0624* (2013.01); *A61N 2/002* (2013.01); *A61N 2/004* (2013.01);
  (Continued)

(58) Field of Classification Search
  CPC ...... A61N 5/0624; A61N 2/002; A61N 2/004; A61N 2005/0662; A61N 2005/0659; A61N 2005/0645
  (Continued)

(56) References Cited

U.S. PATENT DOCUMENTS 6,872,221 B2 *    3/2005    Lytle .................... A61N 5/0616
                                                  128/898
7,033,381 B1 *    4/2006    Larsen ................. A61N 5/0616
                                                  607/88

(Continued)

FOREIGN PATENT DOCUMENTS

WO    2006076506 A2    7/2006

OTHER PUBLICATIONS

International Search Report dated Nov. 20, 2012 in related International Patent Application No. PCT/IB2012/053352.

*Primary Examiner* — Michael Carey

(57) ABSTRACT

Methods and devices of treating fungal nail infections are disclosed. A portable device for treating fungal nail infections includes an irradiator configured to irradiate light of at least first and second types, and an attaching element configured to attach the irradiator to a digit having a nail which is infected by a fungal infection, and to position the irradiator at a position suitable to irradiate at least part of the nail.

25 Claims, 9 Drawing Sheets

Related U.S. Application Data

(60) Provisional application No. 61/504,212, filed on Jul. 3, 2011.

(52) U.S. Cl.
CPC ............. *A61N 2005/0645* (2013.01); *A61N 2005/0659* (2013.01); *A61N 2005/0662* (2013.01)

(58) Field of Classification Search
USPC .............................................. 607/88, 89, 91
See application file for complete search history.

(56) References Cited

U.S. PATENT DOCUMENTS

| | | | |
|---|---|---|---|
| 7,559,945 B2* | 7/2009 | Breden | A61N 5/06 128/898 |
| 2005/0075703 A1* | 4/2005 | Larsen | A61N 1/40 607/88 |
| 2006/0206173 A1 | 9/2006 | Gertner et al. | |
| 2006/0229690 A1 | 10/2006 | Shanks et al. | |
| 2007/0104664 A1 | 5/2007 | Maltezos et al. | |
| 2007/0208395 A1* | 9/2007 | Leclerc | A61N 5/0616 607/86 |
| 2007/0255266 A1 | 11/2007 | Cumbie et al. | |
| 2008/0058905 A1* | 3/2008 | Wagner | A61N 5/0616 607/88 |
| 2008/0077198 A1* | 3/2008 | Webb | A61N 5/0618 607/88 |
| 2009/0143842 A1 | 6/2009 | Cumbie et al. | |
| 2009/0234270 A1 | 9/2009 | Loebel et al. | |
| 2011/0015549 A1 | 1/2011 | Eckhouse et al. | |

\* cited by examiner

DEVICE AND METHOD OF TREATING FUNGAL NAIL INFECTIONS

CROSS REFERENCE TO RELATED APPLICATIONS

This application is a continuation-in-part of pending International Application Number PCT/IB2012/053352, filed Jul. 2, 2012, which claims the benefit of priority from U.S. Provisional Application No.: 61/504,212, filed Jul. 3, 2011. This application also claims priority from pending UK Patent Application No.: 1223438.1, filed Dec. 27, 2012 in the UK Intellectual Property Office. All of these applications are hereby incorporated by reference in their entireties.

FIELD

The disclosure relates to devices and methods of treating fungal nail infections.

BACKGROUND

Fungal nail infections, e.g., Onychomycosis, may affect one or more nails, e.g., a toenail and/or a fingernail.

SUMMARY OF THE INVENTION

It is one object of the present invention to provide a portable finger clip device for treating fungal nail infections, comprising:
  a. an irradiator configured for irradiating the treated area, comprising at least one blue light emitting diode (LED) as a first light source and at least one IR laser light as a second light source, housed therein;
  b. a power source; and
  c. a controller for controlling the at least one blue (LED) and the at least one IR laser light source;
  wherein the controller is adapted to control the irradiator to generate the red light and/or the blue light according to a suitable frequency scheme; the frequency scheme includes blue light irradiation at a wavelength of between 390 nm and 500 nm and the red light irradiation at a wavelength of between about 600 nm and about 950 nm; further wherein the blue LED source and the IR laser light source are arranged in a geometric array such that the projected beams of the light sources are configured to at least partially overlap the treated area.

It is another object of the present invention to disclose the detailed above device, wherein the blue light is preferably at a wavelength of about 470 nm.

It is another object of the present invention to disclose the detailed above device, wherein the irradiator comprises at least two blue LEDs and one IR laser light to generate blue light with red light relatively; the IR laser light provides low power level of about 25W.

It is another object of the present invention to disclose the detailed above device, wherein the at least one light source comprises a light configured for nail therapy, pain treatment and in parallel therapy of skin surrounding the fungal infection.

It is another object of the present invention to disclose the detailed above device, wherein the red light is preferably at a wavelength of about 905 nm.

It is another object of the present invention to disclose the detailed above device, wherein the frequency scheme includes a first sequence of frequencies increasing linearly and continuously from a first frequency to a second, greater, frequency, and a second sequence of frequencies decreasing linearly and continuously from the second frequency to the first frequency.

It is another object of the present invention to disclose the detailed above device, wherein irradiator is adapted to irradiate first frequency comprising a frequency of about 100 Hertz (Hz), and the second frequency comprising a frequency of about 3000 Hz.

It is another object of the present invention to disclose the detailed above device, wherein at least one of the following holds true:
  a. the irradiator is adapted to irradiate the first light source during a first irradiation period, and substantially and simultaneously to irradiate the second light source during a second irradiation period: the first and second irradiation periods are at least partially overlap; and
  b. the irradiator is used for irradiating the red light and/or the blue light according to a frequency scheme including a first sequence of frequencies increasing continuously from a first frequency to a second, greater, frequency, and a second sequence of frequencies decreasing continuously from the second frequency to the first frequency.

It is one object of the present invention to provide a method of using a device for irradiating an infected fungal nail steps of:
  a. providing a portable finger clip device for treating fungal nail infections, comprising:
    i. an irradiator configured for irradiating the treated area, comprising at least one blue light emitting diode (LED) as a first light source and at least one IR laser light as a second light source, housed therein;
    ii. a power source; and,
    iii. a controller for controlling the at least one blue (LED) and the at least one IR laser light source;
  b. providing a frequency scheme;
  c. positioning the irradiator upon the treated area at a position suitable to irradiate at least partly of the nail; and
  d. operating the irradiator to irradiate light of at least one the blue light source and at least one the red light source on at least a portion of the treated area;
wherein the method additionally comprising steps of irradiating at least one the blue light source and/or at least one the red light source according to a suitable frequency scheme comprising the blue light at a wavelength of between 390 nm and 500 nm and the red light in a wavelength of between 600 nm and 950 nm; the frequency scheme including a first sequence of frequencies increasing linearly and continuously from a first frequency to a second, greater frequency, and a second sequence of the frequencies decreasing linearly and continuously from the second frequency to the first frequency.

It is another object of the present invention to disclose the detailed above method, wherein the steps of irradiating the blue light at a wavelength of about 470 nm.

It is another object of the present invention to disclose the detailed above method, wherein the steps of irradiating the red light at a wavelength of about 905 nm.

It is another object of the present invention to disclose the detailed above method, wherein the method additionally comprising steps of irradiating first frequency of about 100 Hertz (Hz), and second frequency of about 3000 Hz.

It is another object of the present invention to disclose the detailed above method, wherein the step of irradiating the first light source is during a first irradiation period, and the second light source is during a second irradiation period; the first and second irradiation periods at least partially overlap.

It is another object of the present invention to disclose the detailed above method, wherein the method additionally comprising of providing the blue LED source and the IR laser light source, configured to overlap the treated area such that the irradiator emits light in wavelength frequencies at a predetermined treatment power.

It is another object of the present invention to disclose the detailed above method, wherein at least one of the following holds true:
  a. irradiating the red light according to a frequency scheme including a first sequence of frequencies increasing continuously from a first frequency to a second, greater, frequency, and a second sequence of frequencies decreasing continuously from the second frequency to the first frequency; and
  b. irradiating the blue light according to a frequency scheme including a first sequence of frequencies increasing continuously from a first frequency to a second, greater, frequency, and a second sequence of frequencies decreasing continuously from the second frequency to the first frequency;

It is another object of the present invention to disclose the detailed above device, wherein the device further comprising a lower gripping element and an upper gripping element opposed to one another; the lower and upper gripping element are pivotally attached to a spring portion to keep the clip closed around a toe or finger; the clip incorporates at least one blue light LED and at least one IR laser light mounted in the clip for irradiating light toward the nail when the clip is closed around the toe or the finger.

It is another object of the present invention to disclose the detailed above device, wherein the at least one light source comprises a light configured for nail therapy, pain treatment and in parallel skin therapy, surrounding the fungal infection.

It is another object of the present invention to disclose the detailed above device, wherein the device further comprises a separator configured to at least partially separate the irradiator and/or other portions of the device from the treated area.

It is another object of the present invention to disclose the detailed above device, wherein at least one of the following holds true:
  a. the geometric array has a configuration selected from the group consisting of: polygon, square, triangle, hexagon, sphere, hemisphere, cylinder, circle, ellipse, rectangles, T-shape, bow tie or any polygon; and
  b. the geometric array has a three-dimensional (3D) or two-dimensional array configuration.

It is another object of the present invention to disclose the detailed above device, wherein at least one of the following holds true:
  a. said configuration of said geometric array further comprises at least two light source positioned in a pattern selected from the group consisting of: polygon, square, triangle, hexagon, sphere, hemisphere, cylinder, circle, ellipse, rectangles, T-shape, bow tie or any polygon, within the interior of the configuration for distributing light;
  b. the geometric array of the light sources for providing an optimal overlapped light beam on the treated area is adjusted according to variables selected from the group consisting of the position of the light sources, the intensity of the light sources, the distance between light sources, the optimal frequency for treating the treated area; and
  c. the geometry arrangement of the light sources of the laser and at least the one LED are within an acceptance angle adjusted to about 6.9 mm distance between the light sources;

It is another object of the present invention to disclose the detailed above device, wherein the blue light source is with a beam divergence of about 9×25 degrees.

It is another object of the present invention to disclose the detailed above device, wherein the red light source is with a beam divergence of about 120 degrees It is another object of the present invention to disclose the detailed above device, wherein the light sources produce an extended source having average acceptance angle of about 35 mR.

It is another object of the present invention to disclose the detailed above device, wherein the fungal infections are selected from the group consisting of: distal lateral subungual Onychomycosis (DLSO), white superficial Onychomycosis (WSO), proximal subungual Onychomycosis (PSO), endonyx Onychomycosis (EO), and candidal Onychomycosisand any related disorder.

BRIEF DESCRIPTION OF THE DRAWINGS

For simplicity and clarity of illustration, elements shown in the figures have not necessarily been drawn to scale.

DETAILED DESCRIPTION

Figure 1:
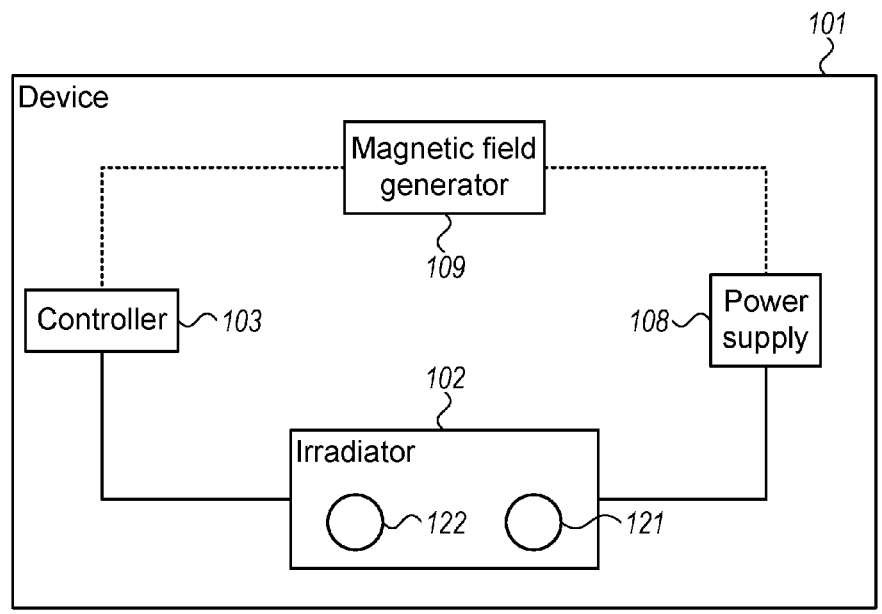
FIG. 1 is a schematic illustration of a device, in accordance with some demonstrative embodiments.

In the following detailed description, numerous specific details are set forth in order to provide a thorough understanding of some embodiments. However, it will be understood by persons of ordinary skill in the art that some embodiments may be practiced without these specific details.

Some demonstrative embodiments may be configured to at least partially treat an area ("the treated area") infected by nail fungus, e.g., Onychomycosis. The treated area may include, for example, at least part of a nail, e.g., a fingernail or a toenail.

Some demonstrative embodiments may include devices, systems and/or methods to enable a non-invasive treatment of the treated area, e.g., as discussed in detail below.

In some demonstrative embodiments, a device of treating fungal nail infections may include an irradiator configured to irradiate the treated area with light of at least two types, e.g., light of two different wavelengths and/or light of different colors.

The term "fungal nail infection" specifically applies hereinafter to Onychomycosis also known as "Dermatophytic Onychomycosis," "Ringworm of the nail," and "Tinea unguium "Distal subungual onychomycosis", "White superficial onychomycosis" (WSO), "Proximal subungual onychomycosis", "Candidal onychomycosis" or any other disorder or disease related to fungal infection of toenails or fingernails.

In some demonstrative embodiments, a first type of light may be configured to at least partially eliminate and/or destroy the nail fungal infection. A second type of light may be configured for skin therapy of the treated area, for example, by increasing and/or enhancing cell therapy and/or cell proliferation in the treated area.

In some demonstrative embodiments, the first type of light may include blue blue light emitting diode (LED) source, for example, light of a wavelength of between 450 nanometer (nm) and 500 nm. The first light source is a blue LED source, with a wavelength of between about 390 nanometer (nm) to about 500 nm, more preferable about 470 nm.

In some demonstrative embodiments, the blue light may destroy infections associated with the nail fungus. For example, a nail infected by nail fungus may be deformed, crumbled and/or broken. As a result, the nail may be vulnerable to different types of injuries, e.g., from hits, wearing tight shoes and/or the like. Such injuries may wound a nail bed and may expose the nail bed to the fungal nail infections. A wounded nail bed combined with the fungal nail infections may be very painful.

In some demonstrative embodiments, irradiating the treated area with the blue light may activate substances called porphoryns. The porphoryns may destroy, at least partially, the fungal nail infection, e.g., without causing substantial damage to the skin in the treated area. In one example, irradiating the treated area with the blue light may damage a DNA structure of the fungal nail infection, which may prevent the fungal nail infection from being able to replicate. In another example, irradiating the treated area with the blue light may create free radicals, which may split bonds between molecules of the fungal nail infection, resulting in at least partially destroying the molecules.

In some demonstrative embodiments, irradiating the treated area with the blue light may have a sanitizing and/or sterilizing effect on the nail bed and may ease and cure one or more symptoms associated with the fungal nail infections. The blue light may be safe for patients of various ages and/or having various health conditions.

In some demonstrative embodiments, the second type of light may include an infrared(IR) laser light source, for example, light of a wavelength of the visible and near infra-red (IR) region of the electromagnetic spectrum, for example, a wavelength of between 600 nm to 950 nm, e.g., 905 nm.

In some demonstrative embodiments, irradiating the skin in the treated area with the red light may increase circulatory flow, enhance lymphatic drainage and/or improve metabolic function of damaged, e.g., infected, injured and/or depressed, cells in the treated area.

The blue LED source and the IR laser light source are arranged in an optimized geometric array such that the projected beams of the light sources are configured to overlap the treated area. The geometric array provides optimal light distribution, such that the irradiator emits light in wavelength frequencies at a predetermined treatment intensity which substantially covers all of the infected area. The geometric array further provides optimal light distribution therapy. The intensity of the blue light is not limited and it can be adjusted to patients of various ages and/or having various health conditions, including regular usage of medicine containing harmful cross-effects with conventional oral or other types of medications. The intensity can be adjusted between 3 W-9 W.

The geometric array structure is determined according to a predetermined angle and distance between the light sources which are selected for higher and improved emission efficacy, There are several possible uniform light patterns such as regular polygons, using squares, triangles or hexagons. The geometric array structure may be spheres, hemispheres, cylinders, or squares arranged as a two-dimensional array. A similar structure that is also in accordance with the present invention is a two-dimensional array shaped as circles, ellipses, squares, rectangles, triangles, or bow ties. The geometric array may further include a three-dimensional (3D) array configuration.

In some demonstrative embodiment, the red light may have a relatively low power level, e.g., a power of 25 Watt (W). Irradiating the red light having the low power level may not cause any side effects, which may be related to using laser of a relatively high power and/or bandwidth, e.g., a wavelength above 1000 nm and/or an ultraviolet light. Therefore, utilizing the red light having the relatively low power level may be safe for use. For example, the red light may not cause any side effects on the skin surrounding the treated area, e.g., burn marks, blisters, scars, redness of skin and/or the like. Moreover, irradiating the treated area with the red light may not cause any pain during and/or after the treatment.

In some demonstrative embodiment, the present invention provides the combination of Low Level Laser Therapy (LLLT) and visible blue light in one device, the energy of which penetrates through the infected nail, targeting fungus spores residing underneath. This combination provides a synergic therapeutic, anti microbial and anti inflammatory effect which traverses the infected nail, and functionally inhibits or destroys or arrests growth of the fungal spores.

The device of the present invention achieves an efficient solution in easing and curing symptoms associated with fungal infection of the nail, both for toenails and for fingernails. The device comprises a low level laser which together with blue light radiation produces a therapeutic effect, curing fungal nail infection both in the feet as well as in the hands. These two different energy modalities, combined together, will produce a symbiotic effect of eliminating Onychomycosis.

The Low-level laser therapy is known as a medical and that uses low-level lasers or light-emitting diodes to alter cellular function. Low level laser therapy is used in the treatment of a broad range of conditions. LLLT improves wound healing, reduces edema, and relieves pain of various etiologies, including successful application to wound and surgical sites to reduce inflammation and pain. The device of the present invention provides LLLT which is further adapted to reduce subject's pain according to pain scale. Pain sacle rates subject's level of pain therefore, measures a patient's pain intensity or other features. Different types of pain scales may further be adapted such as verbal, numerical or visual pain scales. The pain scale which may be used is Wong Baker Faces Pain Scale having the following scale: Face 0 doesn't hurt at all, Face 2 hurts just a little bit, Face 4 hurts a little more, Face 6 hurts even more, Face 8 hurts a whole lot and Face 10 hurts as much as you can imagine. The device of the present invention is with a pain Wong Baker Faces Pain Scale level between face 0 to LLLT is further adapted in the frequencies scheme treatment to repair of injured muscles and tendons. LLLT utilizes low level laser energy, wherein the treatment has a dose rate that causes no immediate detectable temperature rise of the treated tissue and no macroscopically visible changes in tissue structure. Consequently, the treated and surrounding tissue is not heated or damaged, and the patient feels no sensation during treatment. LLLT may further effectively photodestroy a targeted biological element under suitable treatment conditions.

The effects of LLLT is limited to a specified set of wavelengths of laser, and administering LLLT below the dose range does not appear to be effective.

Without wishing to be bound by theory, LLLT may further reduce pain related to inflammation by lowering, in a dose-dependent manner, levels of prostaglandin E2, prostaglandin-endoperoxide synthase 2, interleukin -beta, tumor necrosis factor-alpha, the cellular influx of neutrophil granulocytes, oxidative stress, edema, and bleeding. The appropriate dose appears to be between 0.3 and 19 joules per square centimetre. Another mechanism may be related to stimulation of mitochondrion to increase the production of adenosine triphosphate resulting in an increase in reactive oxygen species, which influences redox signalling, affecting intracellular homeostasis or the proliferation of cells. The final enzyme in the production of ATP by the mitochondria, cytochrome c oxidase, does appear to accept energy from laser-level lights, making it a possible candidate for mediating the properties of laser therapy.

The effects of LLLT is limited to a specified set of wavelengths of laser, and furthermore it is required to determine the ideal wavelengths, durations of treatment, dose and location of treatment. Administering LLLT below the dose range does not appear to be effective. The typical laser average power is in the range of 1-500 mW, some high-peak-power, short-pulse-width devices are in the range of about 1-100 W with typical pulse-widths of 200 ns. Therefore the typical average beam irradiance is then 10 $mW/cm^2$-5 $W/cm^2$. The typical wavelength is in the range of about 600-1000 nm (red to near infrared).

In some demonstrative embodiments, the red light may change the biochemical behavior of adenosine triphosphate (ATP) molecules and may relatively increase the production of ATP. ATP molecules may be the "fuel" that drives protein production, and hence cell proliferation. ATP molecules store chemical energy and release chemical energy to the biochemical processes occurring in the cell. For example, increasing the production of ATP molecules may enhance biological work, which requires chemical energy, e.g., movement, protein synthesis, active transport and/or the like. As a result, irradiating the treated area with the red light may reduce a time period, which is required for growing new and healthy nails. For example, irradiating the treated area with the red light may reduce a treatment time from about 9 months to about 3 months or less.

In some demonstrative embodiments, the device may be configured to generate the red light according to a suitable frequency scheme. For example, the frequency scheme may include frequencies suitable for irradiating various depths of the treated area, e.g., as described below with reference to FIG. 5.

In some demonstrative embodiments, the device may generate the blue and/or red lights according to a suitable irradiation scheme.

In some demonstrative embodiments, the irradiation scheme may define one or more first irradiation periods for irradiating the red light and one or more second irradiation periods for irradiating the blue light.

In some demonstrative embodiments, the first and second irradiation periods may at least partially overlap.

In some embodiments, the device may be configured to irradiate the red and blue lights, substantially simultaneously, for a predefined period of time, for example, about seven minutes, e.g., as described below with reference to FIG. 6.

In other embodiments, the device may be configured to irradiate the red and blue lights during different time periods. For example, the device may be configured to irradiate the red light for a first predefined time period, e.g., 5 minutes, and the blue light for a second predefined period, which may be, for example, different from, e.g., longer than, the first time period. For example, the second time period may include a period of at least 5 minutes. In one example, the first and second time periods may at least partially overlap. For example, the device may simultaneously irradiate the red and blue lights during an initial time period, e.g., five minutes, followed by an additional time period, e.g., about one minute, during which only the blue light is irradiated. In other embodiments, any other suitable irradiation scheme may be utilized.

In some demonstrative embodiments, irradiating the red and blue lights substantially simultaneously may cause a symbiotic effect for treating the fungal nail infection. For example, irradiating the red and blue lights substantially simultaneously may enable reaching deeper depths of the treated area, e.g., compared to the depths reached, when irradiating the blue light or the red light separately. For example, irradiating the red and blue lights substantially simultaneously may enable the red and blue lights to penetrate through an infected nail, e.g., to treat the nail bed.

In some demonstrative embodiments, the device may optionally include a magnetic field generator configured to generate a magnetic field around the treated area. The magnetic field may enhance the treatment to the fungal nail infection. For example, the magnetic field may cause a symbiotic effect for treating the fungal nail infection, in which a penetration of the red and blue lights may be at a deeper depth of the treated area. In other embodiments, the device may not utilize the magnetic field.

In some demonstrative embodiments, the device may be positioned on an outer surface of the treated area. Accordingly, the device may provide a non-intrusive and safe treatment.

In some demonstrative embodiments, the device may include a portable lightweight device. The device may be utilized for home and/or self-treatment. For example, a user having a nail fungal infection may use the device in a favored location, e.g., at home and/or at work, instead of attending a clinic for treatment. The device may be utilized by the user at a convenient time, for example, while staying at home, or while being at work.

In some demonstrative embodiments, the device may be attachable to a finger or a toe, which is infected by nail fungus.

In some demonstrative embodiments, the device may include an attaching element configured to position the irradiator at a position suitable to irradiate the treated area. In one example, the attaching element may include a clip, e.g., as described below with reference to FIG. 2A. In another example, the attaching element may include an elastic strap, e.g., as described below with reference to FIG. 3A. In another example, the attaching element may include an adhesive bandage, e.g., as described below with reference to FIG. 3B. In other examples, the attaching element may include or may be implemented as part of any other suitable element or mechanism capable of positioning the irradiator at a suitable position for irradiating the treated area.

In some demonstrative embodiments, one or more elements of the device, e.g., the irradiator, may be housed within the attaching element, e.g., as described below.

In some demonstrative embodiments, the device may be configured for reuse, e.g., for repeated treatment on the same finger or toe and/or on a different finger or toe of the same user or of a different user.

Fungal nail infections are highly contagious and may be transferred between the fingers and the toes, e.g., between treatments and/or between several infected fingers or toes.

In some demonstrative embodiments, the device may include a separator configured to at least partially separate the irradiator and/or other portions of the device from the treated area.

In some demonstrative embodiments, the separator may include a replaceable separator, which may be replaced between treatments of the same nail and/or between treatments of different nails. Accordingly, the separator may reduce the risk of, or even prevent, contamination by the nail fungi of the treated area.

In some demonstrative embodiments, the device may enable non-invasive treatment of the nail fungal infection without any need to use any traditional medical treatment, e.g., medicines, chemical substances, medical tests, visit at a clinic and follow up visits at the clinic and/or the like.

Reference is now made to FIG. 1, which schematically illustrates a device 101 for treating fungal nail infections, in accordance with some demonstrative embodiments.

In some demonstrative embodiments, device 101 may include an irradiator 102 configured to irradiate a treated area with light of at least two types, e.g., light of two different wavelengths and/or light of different colors.

In some demonstrative embodiments, a first type of light may be configured to at least partially eliminate and/or destroy the fungal nail infection. A second type of light may be configured for skin therapy of the treated area, for example, by increasing and/or enhancing cell therapy and/or cell proliferation in the treated area.

In some demonstrative embodiments, the first type of light may include a blue light, for example, light of a wavelength of between 450 nanometer (nm) to 500 nm, e.g., 470 nm.

In some demonstrative embodiments, the blue light may destroy infections associated with the nail fungus. For example, a nail infected by nail fungus may be deformed, crumbled and/or broken. As a result, the nail may be vulnerable to different types of injuries, e.g., from hits, wearing tight shoes and/or the like. Such injuries may wound the nail bed and may expose the nail bed to the fungal nail infections. A wounded nail bed combined with the fungal nail infections may be very painful.

In some demonstrative embodiments, irradiating the treated area with the blue light may activate substances called porphoryns. The porphoryns may destroy, at least partially, the fungal nail infection, e.g., without causing substantial damage to the skin in the treated area. In one example, irradiating the treated area with the blue light may damage a DNA structure of the fungal nail infection, which may prevent the fungal nail infection from being able to replicate. In another example, irradiating the treated area with the blue light may create free radicals, which may split bonds between molecules of the fungal nail infection, resulting in destroying the molecules, at least partially.

In some demonstrative embodiments, irradiating the treated area with the blue light may have a sanitizing and/or sterilizing effect on the nail bed and may ease and cure one or more symptoms associated with the fungal nail infections. The blue light may be safe for patients of various ages and/or having various health conditions.

In some demonstrative embodiments, device 101 may include at least one blue light source 121 configured to generate the blue light.

In some demonstrative embodiments, blue light source 121 may include at least one blue Light Emitting Diode (LED). For example, the blue LED may generate light of the wavelength of 470 nm.

In some demonstrative embodiments, the second type of light may include a red light, for example light of a wavelength of a visible and near IR region of the electromagnetic spectrum, for example, a wavelength of between 600 nm to 950 nm, e.g., 905 nm.

In some demonstrative embodiments, irradiating the skin in the treated area with the red light may increase circulatory flow, enhance lymphatic drainage and/or improve metabolic function of damaged, e.g., infected, injured and/or depressed, cells in the treated area.

In some demonstrative embodiment, the red light may have a relatively low power level, e.g., a power of 25W. Irradiating the red light having the low power level may not cause any side effects, which may be related to using laser of a relatively high bandwidth, e.g., a wavelength above 1000 nm and/or an ultraviolet light. Therefore, utilizing the red light having the relatively low power level may be safe for use. For example, the red light may not cause any side effects on the skin surrounding the treated area, e.g., burn marks, blisters, scars, redness of skin and/or the like. Moreover, irradiating the treated area with the red light may not cause any pain during and/or after the treatment.

In some demonstrative embodiments, the red light may change the biochemical behavior of ATP molecules and may relatively increase the production of ATP. ATP molecules may be the "fuel" that drives protein production, and hence cell proliferation. ATP molecules store chemical energy and release chemical energy to the biochemical processes occurring in the cell. For example, increasing the production of ATP molecules may enhance biological work, which requires chemical energy, e.g., movement, protein synthesis, active transport and/or the like. As a result, irradiating the treated area with the red light may reduce a time period, which is required for growing new and healthy nails. For example, irradiating the treated area with the red light may reduce a treatment time from about 9 months to about 3 months or less.

In some demonstrative embodiments, device 101 may include, at least one red light source 122 configured to generate the red light.

In some demonstrative embodiments, red light source 122 may include at least one red laser light diode. For example, the red laser light diode may generate light of the wavelength of 905 nm.

In some demonstrative embodiments, red light source 122 may be configured to irradiate the red light at the relatively low power level, e.g., a high peak power of 25 W.

In some demonstrative embodiments, device 101 may include a controller 103 configured to control the functionality and/or the operation of device 101 and/or irradiator 102, e.g., as described below.

In some demonstrative embodiments, controller 103 may control irradiator 102 to generate the red light according to a suitable frequency scheme, e.g., as described below.

In some demonstrative embodiments, a depth of the treated area affected by the red light may depend on the frequency of the red light. For example, red light at a first frequency may affect an area at a first depth, and red light at a second frequency, greater than the first frequency, may affect an area at a second depth, lesser than the first depth.

In some demonstrative embodiments, controller 103 may control irradiator 102 to generate the red light according to a frequency scheme configured to irradiate the treated area with the red light throughout a predefined range of depths, e.g., as described below.

Figure 5:
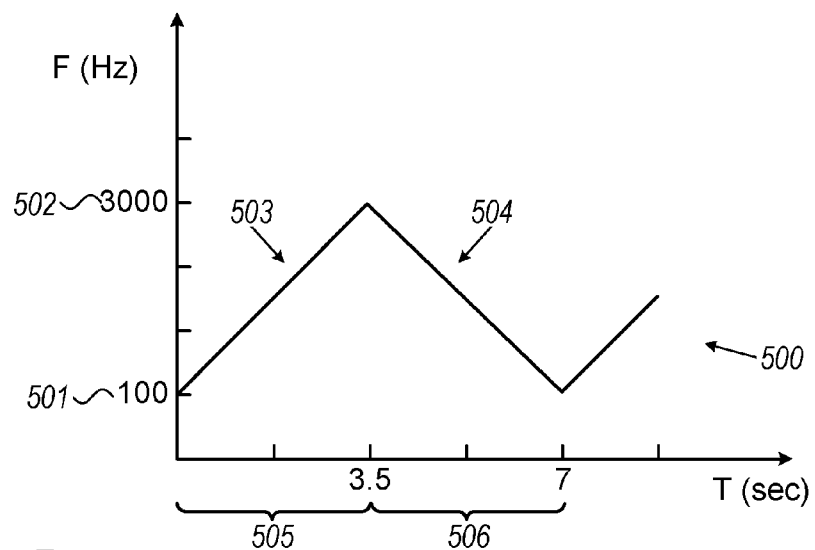
FIG. 5 is schematic illustration of a frequency scheme, in accordance with some demonstrative embodiments.

Reference is now made to FIG. 5, which schematically illustrates a frequency scheme 500, in accordance with some demonstrative embodiments. In some demonstrative embodiments, frequency scheme 500 may be implemented by device 101 (FIG. 1).

As shown in FIG. 5, frequency scheme 500 may include a first sub-sequence 503 of frequencies, e.g., increasing continuously, from a first frequency 501, e.g., 100 Hertz (Hz), to a second frequency 502, e.g., 3000 Hz, during a predefined time period 505, e.g., 3.5 seconds.

As shown in FIG. 5, sub-sequence 503 may be followed by a second sub-sequence 504 of frequencies, e.g., decreasing continuously, from second frequency 502, e.g., 3000 Hz, to first frequency 501, e.g., 100 Hz, during a predefined time period 506, e.g., 3.5 seconds.

In some demonstrative embodiments, frequency scheme 500 may be repeated, e.g., throughout at least a portion of an irradiation period for irradiating the red light. For example, controller 103 (FIG. 1) may control red light source 122 (FIG. 1) to generate the red light according to frequency scheme 500, which may be repeated, for example, throughout a red-light irradiation period.

Referring back to FIG. 1, in some demonstrative embodiments, controller 103 may control irradiator 102 to generate the blue and/or red light according to a suitable irradiation scheme, e.g., as described below.

In some demonstrative embodiments, the irradiation scheme may define one or more first irradiation periods for irradiating the red light and one or more second irradiation periods for irradiating the blue light.

In one example, controller 103 may control red light source 122 and blue light source 121 to irradiate the red and blue lights, substantially simultaneously, for a predefined period of time, e.g., about seven minutes, or any other predefined period.

In another example controller 103 may control red light source 122 to irradiate the red light for a first predefined time period, and control light blue source 121 to irradiate the blue light for a second predefined period, which may be, for example, different from, e.g., longer than, the first time period.

In some demonstrative embodiments, the first and second irradiation periods may at least partially overlap.

Figure 6:
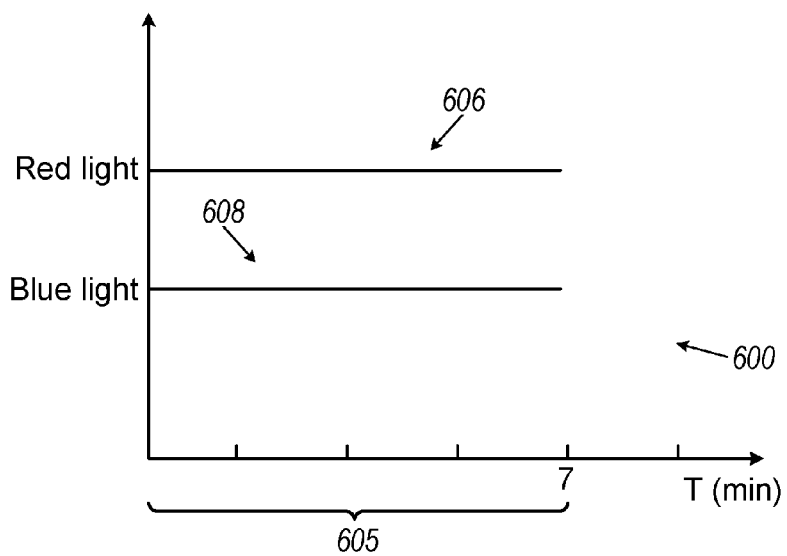
FIG. 6 is schematic illustration of an irradiation scheme, in accordance with some demonstrative embodiments.

Reference is now made to FIG. 6, which schematically illustrates an irradiation scheme 600, in accordance with some demonstrative embodiments.

In some demonstrative embodiments, for example, controller 103 (FIG. 1) may control irradiator 102 (FIG. 1) to generate the blue and/or red light according to irradiation scheme 600.

As shown in FIG. 6, for example, irradiation scheme 600 may include a first irradiation period 608 for irradiating the red light and a second irradiation period 606 for irradiating the blue light.

As shown in FIG. 6, for example, both periods 606 and 608 may be aligned to begin at substantially the same time, such that the red and the blue lights may be irradiated, substantially simultaneously, during a time period 605, e.g., of seven minutes.

Referring back to FIG. 1, in some demonstrative embodiments irradiator 102 may include any suitable combination of one or more light sources. In one example, irradiator 102 may include three red light sources 122 and one blue light source 121 e.g., as described below with reference to FIGS. 2B and/or 4C.

In some demonstrative embodiments, device 101 may optionally include a magnetic field generator 109 configured to generate a magnetic field around the treated area. The magnetic field may enhance the treatment to the fungal nail infection. For example, the magnetic field may cause a symbiotic effect for treating the fungal nail infection, in which a penetration of the red and blue lights may be at a deeper depth of the treated area. In other embodiments, device 101 may not utilize the magnetic field.

In some demonstrative embodiments, device 101 may include a power supply unit 108 configured to supply power required for the operation of device 101, e.g., to provide electric power to light sources 121 and/or 122, to controller 103 and/or to any other suitable element of device 101, e.g., to a user interface as described below. Power supply unit 108 may include any suitable portable power supply unit, e.g., a battery, a rechargeable battery, and the like. In other embodiments, device 101 may receive electric power from an outer supply source, e.g., via a suitable electric connector.

Figure 2A:
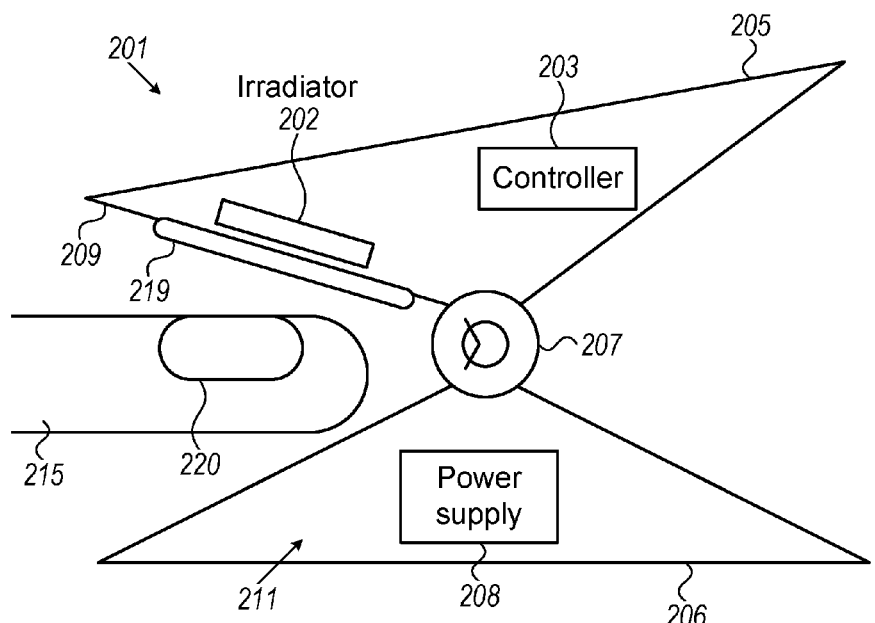
FIGS. 2A and 2B are schematic illustrations of a device of treating fungal nail infections and an engagement portion of the device, in accordance with some demonstrative embodiments.
Figure 2B:
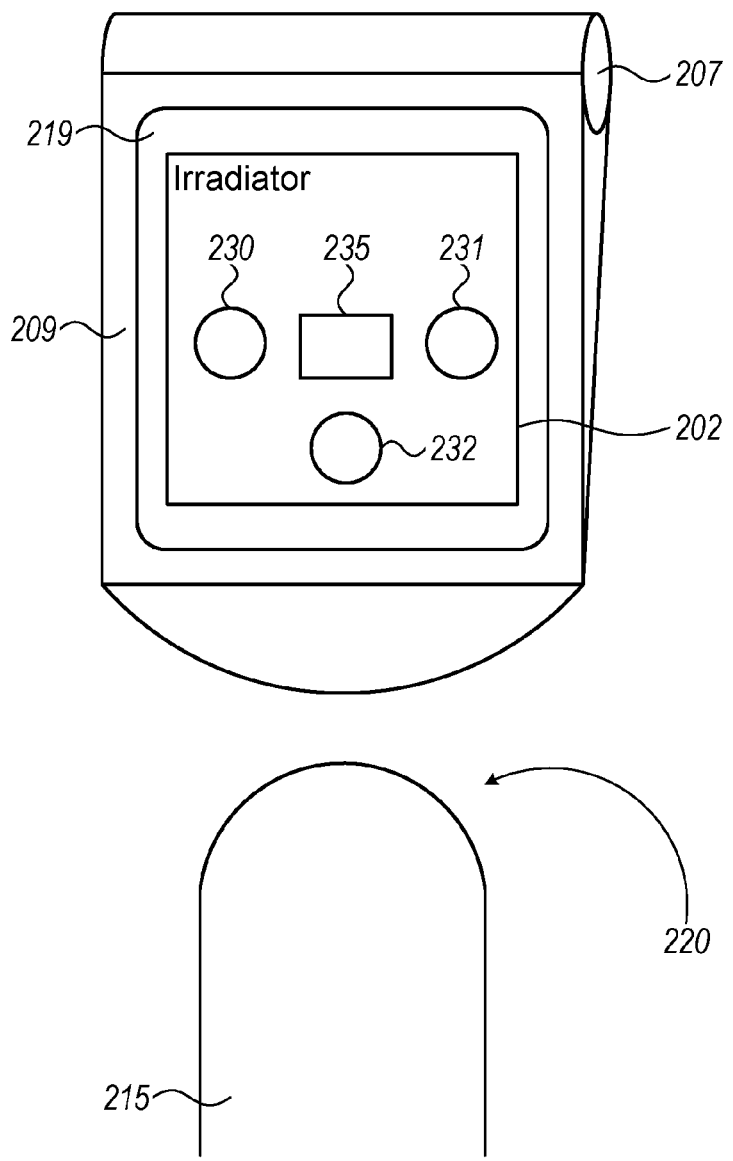

Reference is now made to FIG. 2A, which schematically illustrates a device 201 for treating fungal nail infections, and to FIG. 2B, which schematically illustrates an engagement portion 209 of device 201, in accordance with some demonstrative embodiments. In some embodiments, device 201 may perform the functionality of device 101 (FIG. 1).

In some demonstrative embodiments, device 201 may include an irradiator 202. For example, irradiator 202 may perform the functionality of irradiator 102 (FIG. 1).

In some demonstrative embodiments, engagement portion 209 may be configured to enable irradiator 202 to irradiate treated area 220, e.g., as described below.

In some demonstrative embodiments, device 201 may be formed in a shape of a clip 211 configured to position and/or maintain irradiator 202 at a suitable position to irradiate a treated area 220. The device of the present invention is a portable and in parallel wearable device upon a finger or toe for non-invasive treatment of fungal nail infections.

In some demonstrative embodiments, the structure of the device may further include circular designs, ring designs, clip designs, C-shaped designs, sock designs, thimble designs, cup-like designs that wrap the whole finger or glove finger designs.

In some demonstrative embodiments, the device is easy to carry such that it may further be adapted as a key chain, ring or the like.

In some demonstrative embodiments, clip 211 may be configured to grip a digit 215, e.g., a finger or a toe. Attaching device 201 to digit 215 may increase user comfort, for example, by enabling the user to perform various daily activities without any substantial interference.

In some demonstrative embodiments, device 201 may be formed of any suitable material configured to perform the functionality of a clip, e.g., any suitable plastic material and/or rubber material and the like. One or more elements of device 201 may be housed within clip 211. For example, irradiator 202 may be housed within clip 211, e.g., as described below.

In some demonstrative embodiments, device 201 may include a pair of gripping elements, e.g., a first gripping element 205 and a second gripping element 206 pivotally connected, e.g., in order to enable gripping of digit 215. First gripping element 205 may be configured to engage a portion, e.g., an upper portion, of digit 215, including treated area 220. Second gripping element 206 may be configured to engage an opposite side of digit 215, e.g. a lower portion of digit 215.

In some demonstrative embodiments, device 201 may include a hinge spring 207 positioned between first gripping element 205 and second gripping element 206. Hinge spring 207 may be configured to maintain gripping elements 205 and 206 in a closed position, e.g., tight around digit 215. For example, the user may simultaneously press gripping elements 205 and 206 to pivotally separate gripping elements 205 and 206, e.g., to enable placing of digit 215 to be placed between gripping elements 205 and 206.

In some demonstrative embodiments, device 201 may be formed in a shape configured to firmly maintain digit 215. For example, gripping element 205 may be curved in a shape of an arch, e.g., corresponding to an outer surface of digit 215.

In some demonstrative embodiments, an inner surface of device 201, e.g., an area surrounding digit 215 may be made from any suitable material configured to enable a convenient and comfortable use of device 201. For example, the inner surface may be made of a soft rubber gasket and/or the like.

In some demonstrative embodiments, device 201 may include a separator element 219 configured to at least partially separate irradiator 202 and/or other elements of device 201 from treated area 220. Separator 219 may be positioned between device 201 and treated area 220. For example, separator 219 may cover engagement portion 209. Separator 219 may be used to prevent, or reduce the chances of, the fungal nail infection being transferred from treated area 220 to engagement surface 209, e.g., if device 202 is reused for treating the same treated area 220 or another treated area, of the same user or of another user, e.g., as described above.

In some demonstrative embodiments, separator 219 may be formed of any suitable transparent material, e.g., plastic, tracing paper and the like, for example, to enable the irradiation from irradiator 202 to reach treated area 220. For example, separator 219 may be configured to transmit the light irradiated by irradiator 202 to treated area 220, e.g., without substantially affecting the irradiated light.

In some demonstrative embodiments, separator 219 may include a replaceable separator, which may be replaced between treatments of the same nail and/or between treatments of different nails of the same user r of different users.

In some demonstrative embodiments, device 201 may include a controller 203 housed within gripping element 205. For example, controller 203 may perform the functionality of controller 103 (FIG. 1).

In some demonstrative embodiments, device 201 may include a power supply unit 208 housed within gripping element 206. For example, supply unit 208 may perform the functionality of power supply unit 108 (FIG. 1).

In some demonstrative embodiments, device 201 may be configured to prevent the exposure of the user or another person, e.g., the eyes of the user or another person, to the irradiation generated by irradiator 202, for example, when device 201 is not engaged with treated area 220, e.g., for reasons of safety. For example, device 201 may prevent direct exposure of the eyes of the user to the red light generated by irradiator 202.

In some demonstrative embodiments, device 201 may be configured to disconnect power supply unit 208 from irradiator 202 and/or from one or more light sources of irradiator 202, e.g., when griping element 205 is opened apart from gripping element 206 at an opening angle, which is equal to or greater than a predefined opening angle.

In some demonstrative embodiments, irradiator 202 may be configured to irradiate treated area 220 with light of at least two types, e.g., light of two different wavelengths and/or light of different colors.

In some demonstrative embodiments, the combination of the red laser light source with the blue LED source confers a synergistic effect on the treated area when compared to the therapeutic effect of only a blue LED source.

In some demonstrative embodiments, a first type of light may include at least one blue light and a second type of light may include at least one red light, e.g., as described above with reference to FIG. 1.

As shown in FIG. 2B, for example, in some demonstrative embodiments irradiator 202 may include three light sources 230, 231 and 232 of the first light type, e.g., the blue light. Light sources 230, 231 and 232 may perform the functionality of blue light source 121 (FIG. 1).

As shown in FIG. 2B, for example, in some demonstrative embodiments, irradiator 202 may include a light source 235 of the second light type, e.g., the red light. Light source 235 may perform the functionality of red light source 122 (FIG. 1).

In some demonstrative embodiments, light sources 230, 231 and 232 may be arranged in a shape of a triangle, e.g., having each light source 230, 231 and 232 located in a respective edge of the triangle as shown in FIG. 2B.

In some demonstrative embodiments, light source 235 may be located at the center of the triangle, e.g., as shown in FIG. 2B.

In other embodiments, irradiator 202 may include any other suitable combination of light sources, for example, two red light sources and four blue light sources, and the like. The blue and red light sources may be arranged in any suitable arrangement, e.g., in the form of a rectangle, a circle, and the like.

As shown in FIG. 2B, in some demonstrative embodiments separator 219 may be placed over engagement portion 209 to at least partially cover light sources 230, 231, 232 and 235, and/or engagement portion 209, e.g., as described above.

Figure 3A:
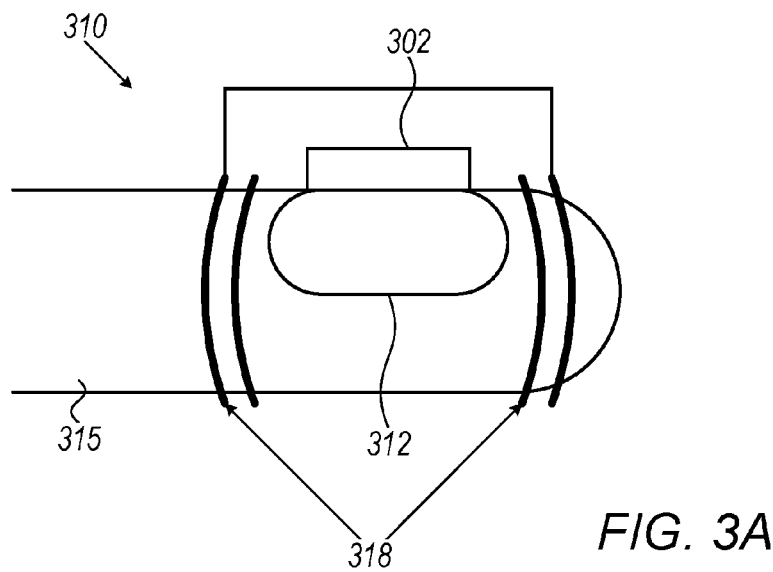
FIGS. 3A and 3B are schematic illustrations of two different configurations of a device of treating fungal nail infections, in accordance with some demonstrative embodiments.
Figure 3B:
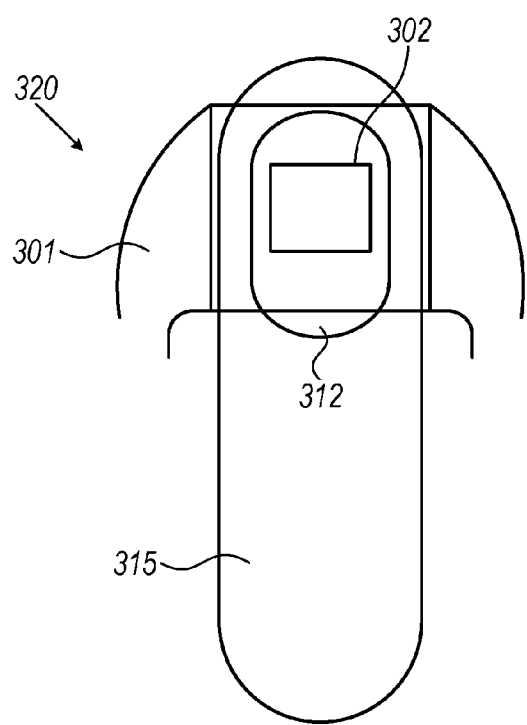

Reference is now made to FIGS. 3A and 3B which schematically illustrate different configurations of a device of treating fungal nail infections, e.g., a device 310 and a device 320, in accordance with some demonstrative embodiments. For example, devices 310 and/or 320 may perform the functionality of device 101 (FIG. 1).

As shown in FIG. 3A, in some demonstrative embodiments, device 310 may be positioned on a treated area 312 using a strap 318 configured to maintain an irradiator 302, e.g., corresponding to irradiator 101 (FIG. 1), at an orientation suitable to irradiate treated area 312. Strap 318 may be connected to both sides of device 310. Strap 318 may tighten and/or maintain device 310 in location, e.g., placed over treated area 312, to enable treatment of treated area 312. Strap 318 may be implemented using any suitable material, for example, an elastic material, e.g., rubber, and/or any other suitable material, e.g., Velcro, or the like.

As shown in FIG. 3B, in some demonstrative embodiments, device 320 may be implemented in the form of an adhesive bandage 301. Bandage 301 may be configured to adhere to a digit 315. For example, irradiator 302 and/ or one or more other elements of device 320 may be implemented in a reduced size, e.g., a size of a nail, a finger or a toe. For example, irradiator 302 and/ or one or more other elements of device 320 may be implemented on an integrated chip (IC), which may be attached to bandage 301. A suitable adhesive material, e.g., adhesive tape, may be utilized to secure irradiator 302 to digit 315.

Figure 4A:
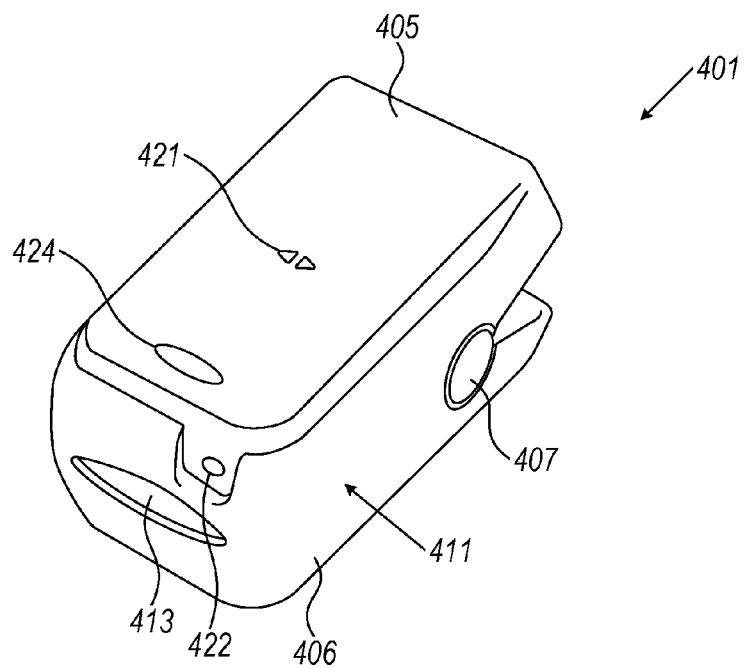
FIGS. 4A, 4B and 4C are schematic illustrations of an isometric view of a device of treating fungal nail infections, a utilization of the device on a toe or finger nail of a user and an electronic circuit of the device, respectively, in accordance with some demonstrative embodiments.
Figure 4B:
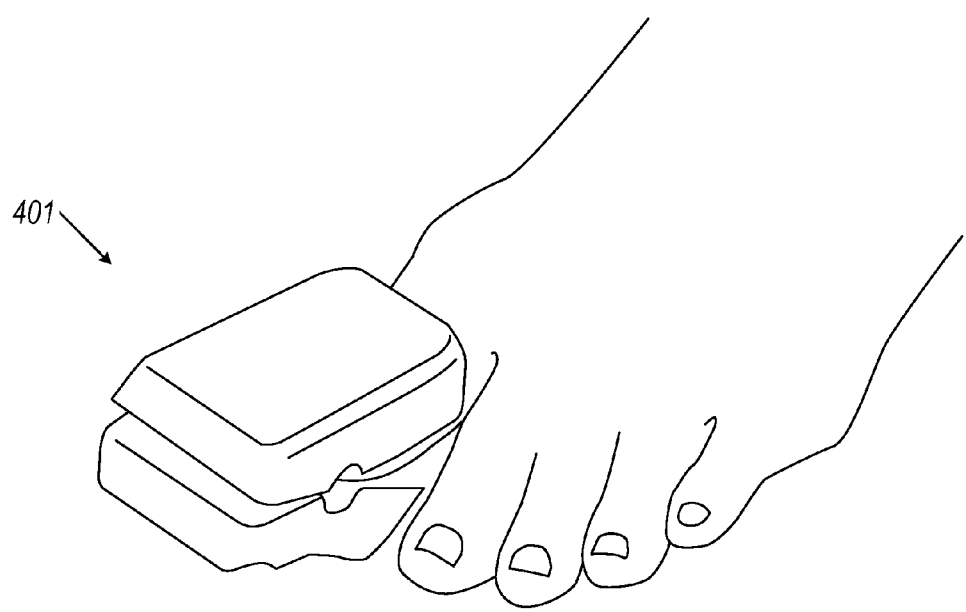
Figure 4C:
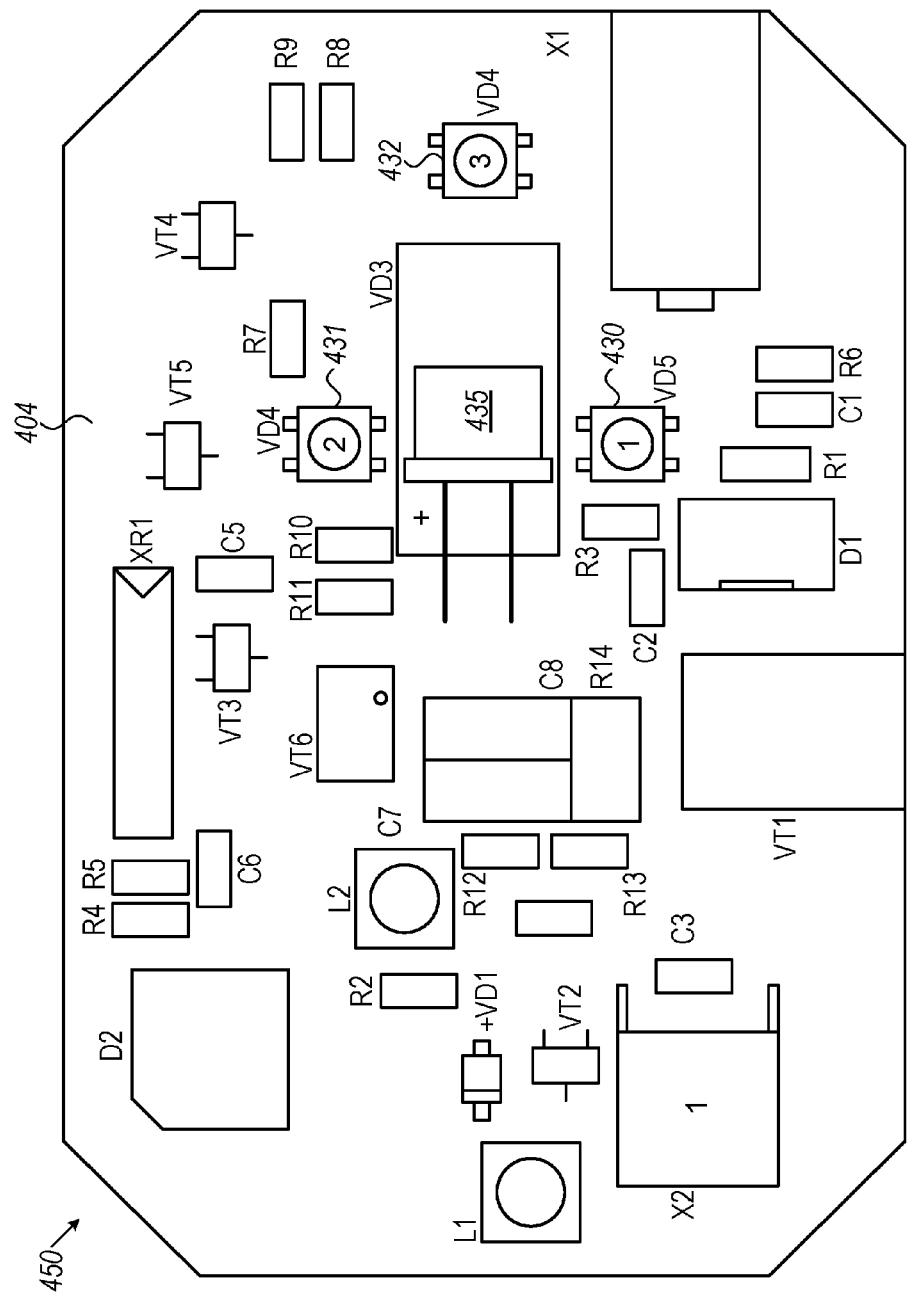

Reference is now made to FIG. 4A, which schematically illustrates an isometric view of a device 401 for treating fungal nail infections, to FIG. 4B, which schematically illustrates utilization of device 401 on a toenail of a user, and to FIG. 4C, which schematically illustrates an electronic circuit 450 of device 401, in accordance with some demonstrative embodiments. In some demonstrative embodiments, device 401 may perform the functionality of device 201 (FIG. 2).

In some demonstrative embodiments, device 401 may be formed in a shape of a clip 411 configured to grip a finger or a toe, e.g., as shown in FIG. 4B. One or more elements of device 401 may be housed within clip 411, e.g., as described below. For example, clip 411 may perform the functionality of clip 211 (FIG. 2A).

In some demonstrative embodiments, clip 411 may include a pair of gripping elements, for example, a first gripping element 405 and a second gripping element 406, which may be pivotally connected. For example, gripping elements 405 and 406 may perform the functionality of gripping elements 205 and 206, respectively (FIG. 2A).

In some demonstrative embodiments, device 401 may include a hinge spring 407 positioned between gripping elements 405 and 406. Hinge spring 407 may be configured to maintain gripping elements 405 and 406 in a closed position. For example, hinge spring 407 may perform the functionality of hinge spring 207 (FIG. 2A).

In some demonstrative embodiments, device 401 may be formed in a shape configured to grip a toe or a finger of a user. For example, gripping element 406 may be curved in a shape of an arch 413, corresponding to a shape of an outer surface of digit 215 (FIG. 2A).

In some demonstrative embodiments, device 401 may include a controller, e.g., housed within gripping element 405. For example, the controller may perform the functionally of controller 203 (FIG. 2A).

In some demonstrative embodiments, device 401 may include a user interface configured to enable the user to operate device 401 and/or to indicate to the user a mode of operation of device 401.

In some demonstrative embodiments, the user interface of device 401 may include an on/off power button 424 configured to operate device 401, e.g., to switch device 401 between a first mode ("on") and a second mode ("off"). Power button 424 may include any suitable button, switch or the like.

In some demonstrative embodiments, device 401 may switch to the second mode automatically, e.g., without any intervention of a user of device 401. For example, device 401 may switch device 401 to the "off" mode after a predefined time period after turning on device 401, e.g., 7 minutes.

In some demonstrative embodiments, the user interface of device 401 may include at least one indicator 421. Indicator 421 may be configured to indicate the mode of operation of device 401 and/or a mode of operation of one or more light sources of device 401. For example, device 401 may include two separate indicators, e.g., a first indicator which may indicate an operational mode of the blue light source, and a second indicator which may indicate an operational mode of the red light source. Indicator 421 may include any suitable indicator, e.g., a two-color LED, and the like.

In some demonstrative embodiments, device 401 may include a power supply unit, e.g., housed within gripping element 406. For example, the power supply unit may perform the functionally of power supply unit 208 (FIG. 2A).

In some demonstrative embodiments, device 401 may include a battery charger connector 422, configured to be connected to an external battery charger, e.g., in order to charge the power supply unit. Charging the power supply unit may be implemented using any suitable method, e.g., via wireless charging and/or a charging pad.

In some demonstrative embodiments, device 401 may be configured to prevent the exposure of the user of device 401 or another person, e.g., the eyes of the user or another person, to the irradiation generated by device 401, for example, when device 401 is not engaged with the treated area, e.g., for reasons of safety.

As shown in FIG. 4C, in some demonstrative embodiments electronic circuit 450 may include a laser diode 435 configured to generate the red light. Laser diode 435 may perform the functionality of red light source 122 (FIG. 1).

In some demonstrative embodiments, electronic circuit 450 may include three blue LEDs 430, 431 and 432, configured to generate the blue light, e.g., blue LEDs 430, 431 and 432 may perform the functionality of blue light source 121 (FIG. 1).

In some demonstrative embodiments, electronic circuit 450 may include a main board 404 configured to electrically connect between elements of device 401. Electronic circuit 450 may include for example, suitable electronic elements, e.g., resistors, capacitors, diodes and/or transistors, for example, as listed in the following table:

TABLE 1

| Part number | Name | Qty | Remarks |
|---|---|---|---|
| | Capacitors | | |
| C1 | CHIP-0603-X7R-4.7 mkF-10 V | 1 | |
| C2 | CHIP-0603-X7R-0.1 mkF-50 V | 1 | |
| C3 | CHIP-0603-X5R-10 mkF-6.3 V | 1 | |
| C4 | CHIP tantalum-C case-220mkF-6.3 V | 1 | |
| C5 | CHIP-0603-X7R-4.7 mkF-6.3 V | 1 | |
| C6 | CHIP-0603-X7R-0.1 mkF-50 V | 1 | |
| C7 | CHIP-1206-Y5V-4.7 mkF-50 V | 1 | |
| C8 | CHIP-1206-0.1 mkF-50V (CL31B104KBCNNNC) | 1 | SAMSUNG |

TABLE 1-continued

| Part number | Name | Qty | Remarks |
|---|---|---|---|
| | Integrated Circuit | | |
| D1 | ADP2291ARMZ (MSOP-8) | 1 | Analog Devices, Inc |
| D2 | PIC16F1827-I/ML (QFN-28) | 1 | Microchip Technology, Inc |
| G1 | Li-Polymer Battery LP753048 | 1 | EEMB Co., Ltd |
| L1 | CHIP inductors SH3018 100YL | 1 | ABC Taiwan Electronics |
| L2 | CHIP inductors SH3018 470YL | 1 | ABC Taiwan Electronics |
| | Resistors | | |
| R1 | CHIP-0805-0.22 Om +− 1% | 1 | |
| R2 | CHIP-0603-130 kOm +− 5% | 1 | |
| R3 | CHIP-0603-200 kOm +− 5% | 1 | |
| R4 | CHIP-0603-20 kOm +− 1% | 1 | |
| R5 | CHIP-0603-15 kOm +− 1% | 1 | |
| R6 | CHIP-0603-470 Om +− 5% | 1 | |
| R7-R9 | CHIP-0805-75 Om +− 5% | 3 | |
| R10 | CHIP-0603-2.2 Om +− 5% | 1 | |
| R11 | CHIP-0603-470 Om +− 5% | 1 | |
| R12 | CHIP-0603-10 kOm +− 5% | 1 | |
| R13 | CHIP-0603-130 kOm +− 5% | 1 | |
| R14 | CHIP-1206-620 kOm +− 5% | 1 | |
| S1 | Tactics button TSQGA-T-1.5 H = 1.5 mm | 1 | TOP-UP CORP |
| VD1 | Diode PMEG2010EJ. (SOD323F) | 1 | |
| VD2 | BI-COLOR Red/Green LED KPB-3025SURKCGKC | 1 | Kingbright |
| VD3-VD5 | BLU LED ET-3528B-A11W | 4 | Edison Opto |
| VD6 | Diode MBR0540T1 (SOD-123) | 1 | |
| VD7 | Laser Diode SPL PL90-3 | 1 | OSRAM |
| VT1 | Transistor PBSS5540Z (SOT-223) | 1 | Termal area |
| VT2 | Transistor IRLML6346TR (SOT-23) | 1 | |
| VT3-VT5 | Transistor IRLML6401TR (SOT-23) | 3 | |
| VT6 | Transistor IRF7752TR (TSSOP-8) | 1 | |
| X1 | Plug TPJ338S-SMT | 1 | TOP-UP CORP |
| X2 | Plug DS1066-2MRW6 (2-Pins) | 1 | Connfly Co., Ltd |
| XR1 | Plug DS1025-01-5P6BV2 (5-pins) (2 mm) | 1 | Connfly Co., Ltd absent |

Figure 7:
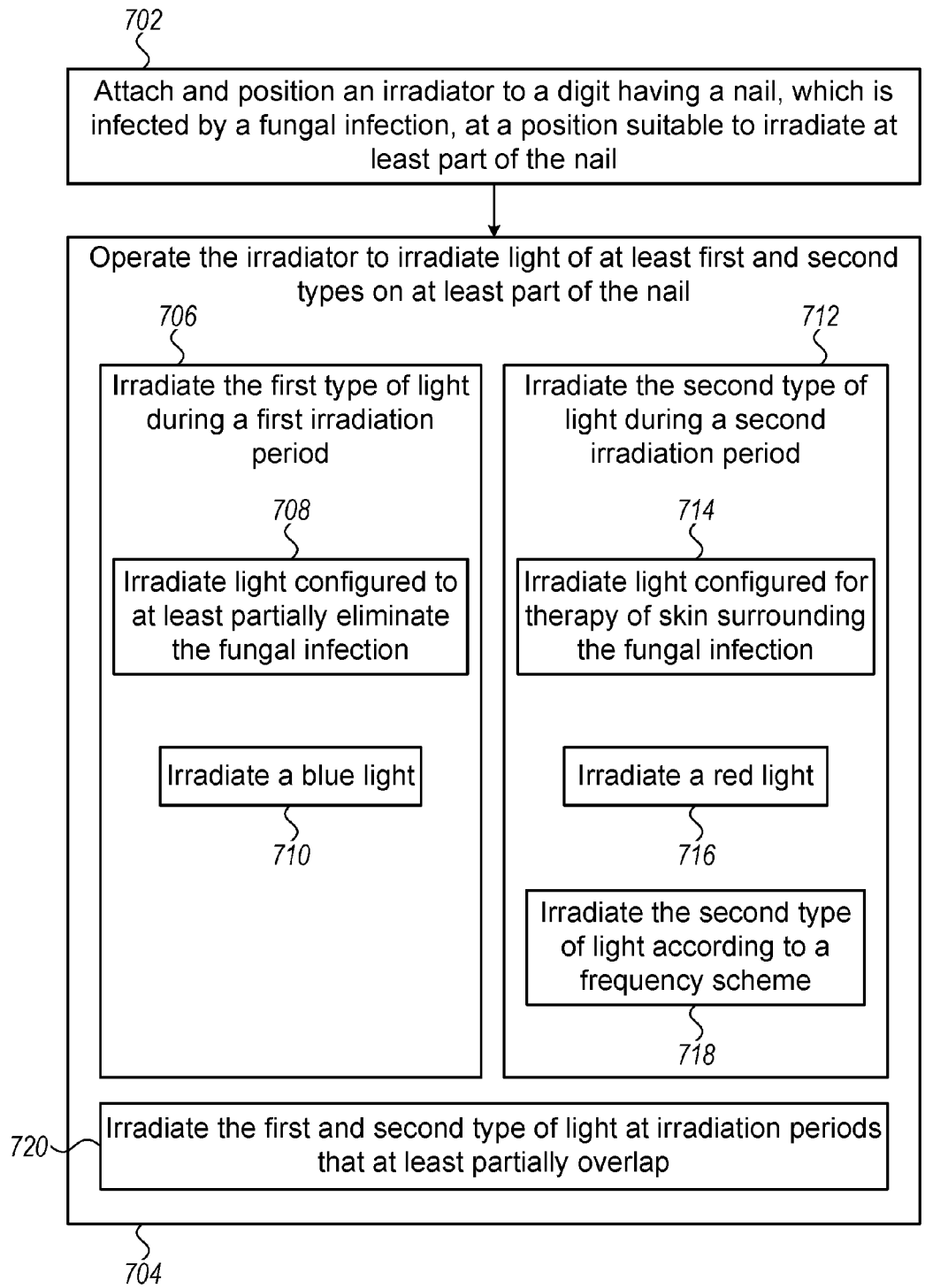
FIG. 7 is a schematic flow-chart illustration of a method of treating fungal nail infections, in accordance with some demonstrative embodiments.

Reference is made to FIG. 7, which schematically illustrates a method of treating fungal nail infections, in accordance with some demonstrative embodiments. In some embodiments, one or more of the operations of the method of FIG. 7, may be performed by any suitable device for treating fungal nail infections e.g., device 101 (FIG. 1), device 201 (FIG. 2A), device 310 (FIG. 3A), device 320 (FIG. 3B) and/or device 401 (FIG. 4A).

As indicated at block 702, the method may include attaching and positioning an irradiator to a digit having a nail, which is infected by a fungal infection, at a position suitable to irradiate at least part of the nail. For example, a user may attach and position irradiator 202 (FIG. 2A) to digit 215 at a position suitable to irradiate treated area 220 (FIG. 2A), e.g., as described above.

As indicated at block 704, the method may include operating the irradiator to irradiate light of at least first and second types on the at least part of the nail. For example, device 201 (FIG. 2A) may operate irradiator 202 (FIG. 2A) to irradiate the light of at least first and second types on treated area 220 (FIG. 2A), e.g., as described above.

As indicated at block 706, operating the irradiator to irradiate the light of at least first and second types may include irradiating the first type of light during a first irradiation period. For example, device 101 (FIG. 1) may irradiate the first type of light during period 606 (FIG. 6), e.g., as described above.

As indicated at block 708, irradiating the first type of light may include irradiating light configured to at least partially eliminate the fungal infection. For example, irradiator 102 (FIG. 1) may irradiate light configured to at least partially eliminate the fungal infection, e.g., as described above.

As indicated at block 710, irradiating the first type of light may include irradiating a blue light. For example, irradiator 102 (FIG. 1) may irradiate the blue light, e.g., as described above.

As indicated at block 712, operating the irradiator to irradiate the light of at least first and second types may include irradiating the second type of light during a second irradiation period. For example, device 101 (FIG. 1) may irradiate the second type of light during period 608 (FIG. 6), e.g., as described above.

As indicated at block 714, irradiating the second type of light may include irradiating light configured for therapy of skin surrounding the fungal infection. For example, irradiator 102 (FIG. 1) may irradiate light configured for therapy of skin surrounding the fungal infection, e.g., as described above.

As indicated at block 716, irradiating the second type of light may include irradiating a red light. For example, irradiator 102 (FIG. 1) may irradiate the red light, e.g., as described above.

As indicated at block 718, irradiating the second type of light may include irradiating the second type of light according to a frequency scheme. For example, irradiator 102 (FIG. 1) may irradiate the second type of light according to frequency scheme 500 (FIG. 5), e.g., as described above.

As indicated at block 720, operating the irradiator to irradiate the light of at least first and second types may include irradiating the first type of light and second type of light at irradiation periods that at least partially overlap. For example, device 101 (FIG. 1) may irradiate the first type of light during period 606 (FIG. 6), and the second type of light during period 608 (FIG. 6), e.g., as described above.

Following is a description of several case studies of treating fungal nail infection. The case studies were conducted by a device of treating fungal nail infections, in accordance with some demonstrative embodiments, e.g., device 102 (FIG. 1).

As demonstrated in the case studies described below, a nail infected by fungal nail infections, which was treated by the device, showed an improvement of the nail health and esthetic appearance after a relatively short period of time, e.g., compared to common treatments of fungal nail infections.

In a first case study, a fungal nail infection caused a nail to become thick and to change color to a mirky yellow. After treating the nail with the device the nail grew to be healthy and the nail appearance returned to normal, e.g., to a normal color and a normal thickness.

In a second case study, a severe fungal nail infection caused a nail color to turn to dark brown-green and a nail plate to become significantly thickened. After treating the nail with the device, a major improvement of the nail health was evident.

In a third case study, a fungal nail infection caused a nail to change a color and a drastic thickening of the nail plate. Results of treatment by the device showed that the color of the nail returned to normal, and the thickness of the nail was decreased.

In a forth case study, a treatment by the device improved a color and clarity of a nail infected by fungal nail infection and decreased a thickness of the nail to a normal thickness.

In a fifth case study, a nail infected by a severe fungal nail infection demonstrated a major improvement of the nail after only 3 weeks of treatment.

In a sixth case study, a nail infected by a severe fungal nail infection, e.g., causing a broken, thick and yellow color nail, demonstrated an improvement after only 13 days of treatment by the device, e.g., a color of the nail was cleared and lightened and a growth of a healthy nail was clearly evident.

Functions, operations, components and/or features described herein with reference to one or more embodiments, may be combined with, or may be utilized in combination with, one or more other functions, operations, components and/or features described herein with reference to one or more other embodiments, or vice versa.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

Figure 8A:
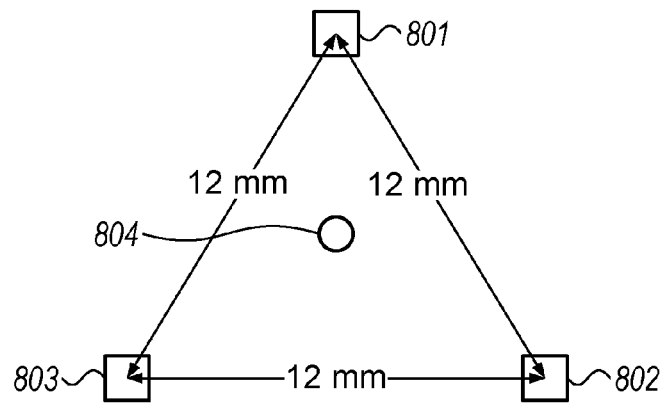
FIG. 8A is schematic illustration of the geometric configuration array of the device of the present invention.

Reference is now made to FIG. 8A, which presents the light sources configuration housed within the irradiator of the device of the present invention. The irradiator contains one infra-red laser source 804 and 3 visible LEDs 801-803 arranged at the geometric structure of a triangle pattern 800. The irradiator may further include any suitable combination of one or more light sources. As shown in FIG. 8A the irradiator includes three LED sources 801,802,803 arranged at the geometric structure in a respective edge of a triangle whilst each LED is in an equal distance away from each other. Furthermore the triangle array comprises at least one red light source 804 located at the center of the triangle configuration 800, forming a triangular-pyramidal array structure. In order to eliminate and/or destroy the nail fungal infection and in parallel to provide skin therapy of the treated area, the desired distance between each led light is of about 12 mm. In order to define the optimized array of several light sources, an arrangement of light sources is selected which provides an optimal overlapped light beam on the treatment surface. The variables are: the position of the light sources, the intensity of the light source, the distance between each light source relative to the optimal geometric arrangement, the Frequency and wavelength adjusted to treat the fungal infection of the treated area.

The optimal radiation pattern of a single light source may be compared to a respective required radiation pattern by calculating a desired distance of the light source from an optical axis of the lighting device.

Other possible uniform light patterns may be adapted such as regular polygons, using squares, triangles or hexagons. The geometric array structure may further be of spheres, hemispheres, bow-ties, cylinders, or squares arranged as a two-dimensional (2D) array. The geometric array may further be a 3D configuration. A similar structure that is also in accordance with the present invention is a two-dimensional array shaped as., circles, ellipses, squares, rectangles, triangles, T-shape or bow ties. The array of light sources is designed to increase the efficiency of the intensity of light treatment upon the treated area. The geometric arrangement of the light sources is specifically configured in a manner for minimizing the heat generated by the device. The geometric arrangement further provides uniform radiation to the treated area, whilst the device configuration further targets uniform light beams to the infected area The geometric arrangement is based upon the inverse-square law which states that the intensity of a specified physical quantity is inversely proportional to the square of the distance from the source of that physical quantity. In equation form:

$$\text{Intensity} \propto \frac{1}{distance^2}$$

This means that the intensity or irradiance of the emitted light or other linear waves radiating from a point source (energy per unit of area perpendicular to the source) is inversely proportional to the square of the distance from the source such that an object twice as far away, receives only one-quarter the energy (in the same time period). More generally, the irradiance, i.e., the intensity (or power per unit area in the direction of propagation), of a spherical wave front varies inversely with the square of the distance from the source (assuming there are no losses caused by absorption or scattering).

In another embodiment of the present invention, the irradiator may comprise any other suitable combination of light sources, for example, two red light sources and four blue light sources, and the like. The blue and red light sources may be arranged in any suitable arrangement, e.g., in the form of a rectangle, a circle, and the like.

In another embodiment of the present invention, the light therapy may be administrated in a pulse therapy manner.

In another embodiment of the present invention at least one pulse parameter is selected from the group consisting of amplitude, pulse duration, a pulse shape, a duty cycle parameter, a pulse sequence parameter, a pulse rise-time, and a pulse frequency.

Light administration of the device of the present invention may be continuous or pulsed, and may be controlled by a controller such as microprocessor. Pulsing of the different light source may treat the affected nail whilst reducing the overall red and blue light exposure to the patient Table 2 presents the laser beams specification

TABLE 2

| Source | λ | Output Power | Pulse energy | Pulse width | PRR | Beam Dimension | Beam Divergence |
| --- | --- | --- | --- | --- | --- | --- | --- |
| Laser | 905 nm | 6 mW | 3 µJ | 100 ns | 2 KHz* | 200 × 2 µm | 9 × 25 deg. |
| LED | 470 nm | 100 mW | Duty cycle 50%** | | | — | 120° |

The laser is operated at Pulse Repetitive Rate (PRR) mode, where the LEDs are taken as a quasi continuous operation. The pulse repetition rate, also known as pulse repetition frequency of a regular train of pulses, is the number of emitted pulses per second, or the inverse temporal pulse spacing. If a pulse train is regular and the pulses are mutually coherent, the optical spectrum of the pulse train is a frequency comb, where the spacing of the lines is determined by the pulse repetition rate.

On the other hand, quasi-continuous-wave (quasi-cw) operation of a laser means that its pump source is switched on only for certain time intervals, which are short enough to reduce thermal effects significantly, but still long enough that the laser process is close to its steady state, i.e. the laser is optically in the state of continuous-wave operation. Therefore, quasi-cw operation allows the operation with higher output peak powers at the expense of a lower average power.

For repetitive pulses the accessible emission limit (AEL) class 1 may be calculated for three cases—Single pulse, Repetitive Pulse and Average power, where the most restrictive case determines the actual AEL. For LEDs the AEL Class 1 is determined by long exposure (average power).

Table 3 presents the calculation formula for the laser and LED light sources.

TABLE 3

| Source | Single Pulse (S.P.) | Repetitive Pulses | Average Power |
|---|---|---|---|
| Laser | $2 \cdot 10^{-7} \, C_4$ J | $S.P \cdot C_5$ | $3.9 \cdot 10^{-4} \, C_4$ W |
| LED | — | — | $3.9 \cdot 10^{-3} \, C_3$ & $3.9 \cdot 10^{-4}$ W |

Where, $C_4$ equal 2.57 for 905 nm C5 equal 0.084 for 2 KHz PRR of a point source $C_3$ (the photochemical coefficient) is 2.5 for 470 nm Substituting the correction factors values in the formulas of Table 3, we get the calculation results presented in Table 4 below.

TABLE 4

| Source | Single Pulse (S.P.) | Repetitive Pulses | Average Power |
|---|---|---|---|
| Laser | $5.14 \cdot 10^{-7}$ J | $4.3 \cdot 10^{-8}$ J/Pulse | $10^{-3}$ W, $5 \cdot 10^{-7}$ J/Pulse |
| LED | | | $3.9 \cdot 10^{-4}$ W * |

The relevant sources that should be taken into account are those within 100 mR angle of acceptance. For a 100 mm distance, 100 mR defines 10 mm length. Using the arrangement geometry of the light sources, as presented in FIG. 8, shows that only the laser and 1 LED could be included within the relevant acceptance angle (6.93 mm distance between them). But those sources (laser+1 LED) produce an extended source having average acceptance angle($\alpha$) of 35.25 mR, thus non point area, resulted in $C_6$ value of 23.5 ($\alpha/1.5$). As a result the AEL of the two sources is multiplied by 23.5, where the total power increases much lower. The bottom line is that the two sources are less hazardous than each one of them. Therefore, the classification of a single source determines all the light sources of the device.

Figure 8B:
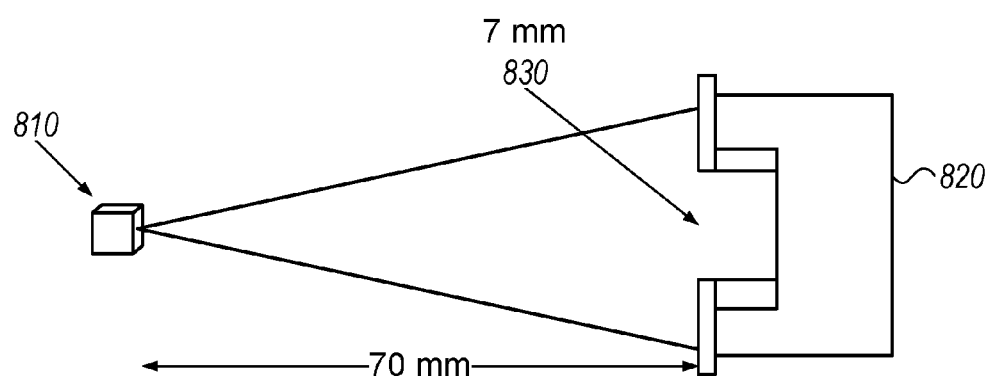
FIG. 8B is schematic illustration of the power effect of the geometry structure of the light sources within the device of the present invention.

Reference is now made to FIG. 8B, which presents the power effect of the geometry structure of the light sources within the device of the present invention. The measurement was taken for the worst case scenario.

The device was tested as follows: a laser radiation detector 820 was placed at 70 mm distance from the light source (LED or laser) whilst a single light source was operated in its normal current and the other 3 were disconnected. The detector 820 was placed with the 7 mm aperture 830 in front of it as close as to the device (worst case), where the device was opened to its largest opening. The device was operated (laser and 3 LEDs (810)) and the results of the measurements are as presented in table 5.

Table 5 below presents the expected power through 7 mm aperture and the measured one, for light sources classification, and the measurement results.

TABLE 5

| | | | | Power Through 7 mm aperture | |
|---|---|---|---|---|---|
| | | AEL | | | |
| Classification | AEL Class 1 | AEL Class 3R | Class 3B | Theory | Measurement |
| Laser | 0.086 mW | 0.43 mW | 500 mW | 1.5 mW | 0.205 mW |
| Single LED | 0.39 mW | 1.96 mW | 500 mW | 0.125 mW | 0.25 mW |
| Product | 5.8 mW | 29 mW | 500 mW | — | 0.105 mW |

As table 5 shows, there are differences between the theory and the power measurements. However, for both theory and measurements the possible exposure level (0.105 mW) is much lower than the AEL class 1 (5.8 mW), whilst the device is assigned Class 1 laser product. Moreover, the light sources are totally enclosed into the protective housing in a way that direct exposure to the light sources is not possible.

The laser light source is encapsulated within the clip configuration of the device of the present invention, which further provides a safer and focused light irradiation. The device is safe to use without any irradiation leakage.

Reference is now made to FIG. 9 which presents a case study, using the present invention, over time with several results of a subject's toe nail as the trial progressed. The study is intended to evaluate the efficacy of a treatment for the condition it is intended to treat; possible side effects are monitored.

FIGS. 9A-9D demonstrate a case study of treating fungal nail infection with the device of the present invention. The case study was conducted by the device of treating fungal nail infections. As demonstrated in the case study described below, a nail infected by fungal nail infections, which was treated by the device, showed an improvement of the nail health and esthetic appearance after a relatively short period of time, compared to common treatments of fungal nail infections.

Figure 9A:
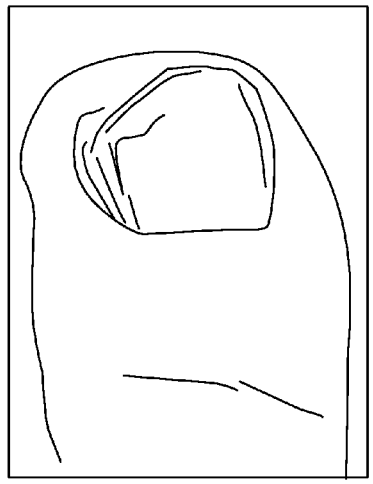
FIG. 9 is a perspective view of a subject's finger/toe nail during treatment using the device of the present invention.

FIG. 9A presents the condition of the subject's toe nail having a fungal nail infection, before starting a treatment.

Figure 9B:
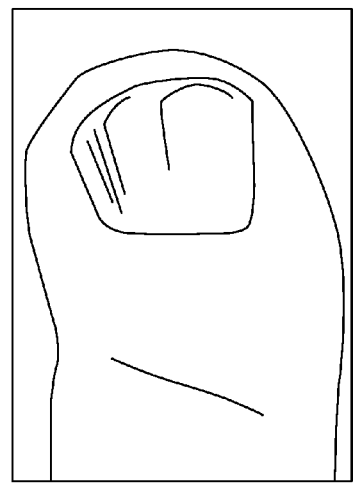

FIG. 9B presents the condition of the subject's toe nail 5 weeks after starting treatment.

Figure 9C:
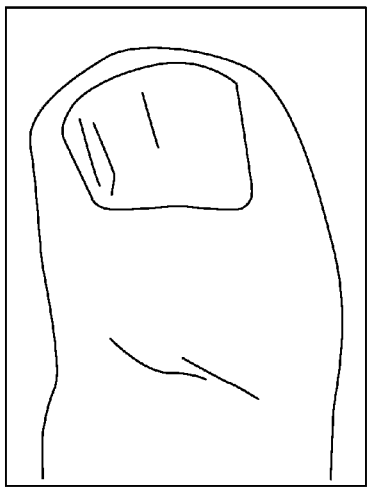

FIG. 9C presents the condition of the subject's toe nail 8 weeks after starting treatment.

Figure 9D:
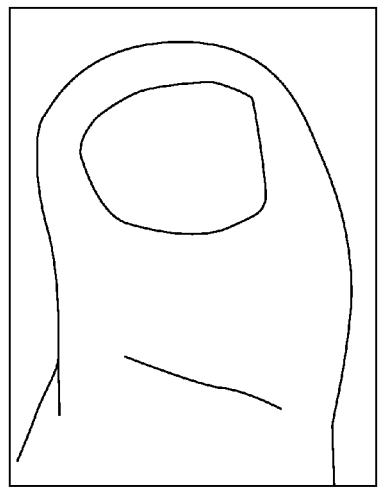

FIG. 9D presents the condition of the subject's toe nail 10 weeks after starting treatment which shows an improvement of the nail health and esthetic appearance after a relatively short period of time.

What is claimed is:
1. A portable finger or toe clip device (101) for treating fungal nail infections, comprising:
an irradiator (102) configured to irradiate a treated area;
a light source comprising at least two blue light emitting diodes (LEDs) (121) and at least one pulsed red laser light source (122), housed within said irradiator and arranged in a geometric array configured to at least partially overlap said treated area;
a power source; and,
a controller interconnecting said power source and said at least two blue LEDs and said at least one pulsed red laser,
said controller configured to control said irradiator such that light radiation from said light source is generated by a combination of light emitted from said at least two blue LEDs at a wavelength between 390 nm and 500 nm and light emitted from said at least one pulsed red laser at a wavelength of between 600 nm and 950 nm in a repetitive mode according to a predetermined frequency scheme;
wherein said frequency scheme comprises a first sequence of frequencies increasing continuously over a first predetermined period of time (505) from a first frequency to a second greater frequency, followed by a second sequence of frequencies decreasing continuously over a second predetermined period of time (506) from said second frequency to said first frequency.

2. The device of claim 1, wherein said at least two blue LEDs are configured to emit light characterized by a wavelength of 470 nm ±10%.

3. The device of claim 1, wherein said pulsed red laser light light source provides a power level of 25 W ±10%.

4. The device of claim 1, wherein said irradiator is usable for nail therapy, pain treatment and in parallel therapy of skin surrounding said fungal infection.

5. The device of claim 1, wherein said pulsed red laser light source is configured to emit light at a wavelength of 905 nm ±10%.

6. The device of claim 1, wherein said first frequency is 100 Hz ±10% and said second frequency is 3000 Hz ±10%.

7. The device of claim 1, wherein at least one of the following is true:
said red light source irradiates during a first irradiation period, said blue light source irradiates during a second irradiation period, said first and second irradiation periods at least partially overlapping; and,
said irradiator is used for irradiating said red light and/or said blue light according to a frequency scheme including a first sequence of frequencies increasing continuously from a first frequency to a second, greater, frequency, and a second sequence of frequencies decreasing continuously from the second frequency to the first frequency.

8. A method of using a device for irradiating an infected fungal nail comprising:
providing a portable finger or toe clip device (101) for treating fungal nail infections, comprising:
an irradiator (102) configured to irradiate a treated, area;
a light source at least two blue light emitting diodes (LEDs) (121) and at least one pulsed red laser light source (122), housed within said irradiator;
a power source; and,
a controller interconnecting said power source and said at least two blue LEDs and said at least one pulsed red laser, said controller configured to control said irradiator such that light radiation from said light source is generated by a combination of light emitted from said at least two blue LEDs at a wavelength between 390 nm and 500 nm and at light emitted from said at least one pulsed red laser at a wavelength of between 600nm and 950 nm in a repetitive mode according to a predetermined frequency scheme;
providing a frequency scheme;
positioning said irradiator upon said treated area at a position suitable to irradiate at least part of said nail; and
positioning said irradiator upon said infected nail at a position suitable to irradiate at least part of said infected nail; and,
operating said irradiator to irradiate light of at least said two blue LEDs and at least one said pulsed red laser light source on at least a portion of said irradiated area;
wherein:
said step of irradiating said area comprises radiating said output of said blue LEDs at a wavelength of between 390 nm and 500 nm and said pulsed red laser light source at a wavelength of between 600 nm and 950 nm, respectively, in a repetitive mode according to said frequency scheme; and,
said step of providing a frequency scheme comprises providing a frequency scheme comprising a first sequence of frequencies increasing continuously over a first predetermined period of time from a first frequency to a second greater frequency, followed by a second sequence of frequencies decreasing continuously over a second predetermined period of time from said second frequency to said first frequency.

9. The method of claim 8, wherein said step of irradiating said area to be treated comprises irradiating by blue light characterized by a wavelength of 470 nm ±10%.

10. The method of claim 8, wherein said step of irradiating said area to be treated comprises irradiating by IR light characterized by a wavelength of 905 nm ±10%.

11. The method of claim 8, wherein said first frequency is 100 Hz ±10%, and said second frequency is 3000 Hz ±10%.

12. The method of claim 8, wherein said step of irradiating by said blue LED is performed during a first irradiation period, and said irradiating by said pulsed red laser is performed during a second irradiation period, and said first and second irradiation periods are at least partially overlapping.

13. The device of claim 1, wherein:
said device further comprises a lower gripping element and an upper gripping element opposed to one another;
said lower and upper gripping element are pivotally attached to a spring portion to keep the clip closed around a toe or finger; and,
said clip incorporates said at least two blue LEDs and said at least one pulsed red laser light source mounted in said clip for irradiating light toward said nail when the clip is closed around said toe or said finger.

14. The device of claim 1, wherein said device further comprises a replaceable transparent separator placeable between said irradiator and said area to be treated, said separator configured for preventing transmission of fungal infection from said area to be treated to another area.

15. The device of claim 1, wherein at least one of the following is true:
said at least two blue light emitting diodes (LEDs) (121) and at least one pulsed red laser light source (122) are arranged in a geometric array characterized by a configuration selected from the group consisting of polygonal, square, triangular, hexagonal, spherical, hemispherical, cylindrical, circular, elliptical, rectangular, T-shaped, bow tie shaped; and,
said at least two blue light emitting diodes (LEDs) (121) and at least one pulsed red laser light source (122) comprise a total of at least four light sources arranged in a pyramidal array.

16. The device of claim 1, wherein at least one of the following is true:

said geometric array of said at least two blue LEDs and at least one pulsed red laser is adjustable for optimizing at least one variable selected from the group consisting of: positions of said at least two blue LEDs and at least one pulsed red laser, intensities of said at least two blue LEDs and at least one pulsed red laser, and distances between said at least two blue LED and at least one pulsed red laser; and, said distance between said at least one pulsed red laser and said at least two blue LEDs is 6.9 mm ±10%.

17. The device of claim 1, wherein said blue LED is characterized by a beam divergence of 9 ×25 degrees ±10%.

18. The device of claim 1, wherein said pulsed red laser is characterized by a beam divergence of 120 degrees ±10%.

19. The device of claim 1, wherein said fungal infection is selected from the group consisting of distal lateral subungual Onychomycosis (DLSO), white superficial Onychomycosis (WSO), proximal subungual Onychomycosis (PSO), endonyx Onychomycosis (EO), and candidal Onychomycosis.

20. The device of claim 1, wherein said device is configured to provide at least one synergistic effect that traverses said infected nail and functionally inhibits, destroys, or arrests growth of fungal spores, said synergistic effect selected from the group consisting of synergistic therapeutic effects, synergistic anti-microbial effects, and synergistic anti-inflammatory effects.

21. The device of claim 1, additionally comprising a magnetic field generator configured to generate a magnetic field around the treated area for enhancing treatment to the fungal nail infection.

22. The device of claim 1, wherein at least one of the following is true:

said first sequence of frequencies increases continuously and linearly over said first predetermined period of time from said first frequency to said second greater frequency; and, said second sequence of frequencies decreases continuously and linearly over said second predetermined period of time from said second frequency to said first frequency.

23. The method of claim 8, wherein at least one of the following is true:

said step of providing a frequency scheme comprises providing a frequency scheme comprising a first sequence of frequencies increasing continuously and linearly over said first predetermined period of time from said first frequency to said second frequency; and, said step of providing a frequency scheme comprises providing a frequency scheme comprising a second sequence of frequencies decreasing continuously and linearly over said second predetermined period of time from said second frequency to said first frequency.

24. The device of claim 1, wherein said pulsed red laser is configured to emit light so as to create a frequency comb.

25. The method of claim 8, wherein said step of irradiating said treated area comprises irradiating said treated area with light emitted from said pulsed red laser as a frequency comb.

* * * * *